US008840612B2

(12) United States Patent
Tontz

(10) Patent No.: US 8,840,612 B2
(45) Date of Patent: Sep. 23, 2014

(54) INTRAOSSEOUS EXPANDABLE FIXATION DEVICE

(76) Inventor: William L. Tontz, San Diego, CA (US)

(*) Notice: Subject to any disclaimer, the term of this patent is extended or adjusted under 35 U.S.C. 154(b) by 0 days.

(21) Appl. No.: 13/464,273

(22) Filed: May 4, 2012

(65) Prior Publication Data
US 2013/0296861 A1 Nov. 7, 2013

(51) Int. Cl.
A61B 17/72 (2006.01)

(52) U.S. Cl.
USPC .......................................................... 606/63

(58) Field of Classification Search
USPC ............. 606/62–68, 313, 326–327, 248–249; 623/23.23
See application file for complete search history.

(56) References Cited

U.S. PATENT DOCUMENTS

| | | | | |
|---|---|---|---|---|
| 3,779,239 | A * | 12/1973 | Fischer et al. | 606/63 |
| 3,986,504 | A * | 10/1976 | Avila | 606/63 |
| 5,176,681 | A | 1/1993 | Lawes et al. | |
| 5,685,826 | A * | 11/1997 | Bonutti | 600/204 |
| 6,224,600 | B1 * | 5/2001 | Protogirou | 606/63 |
| 6,575,973 | B1 * | 6/2003 | Shekalim | 606/62 |
| 6,736,818 | B2 * | 5/2004 | Perren et al. | 606/63 |
| 6,780,185 | B2 * | 8/2004 | Frei et al. | 606/68 |
| 6,922,870 | B2 | 8/2005 | Tontz, Sr. | |
| 7,052,498 | B2 * | 5/2006 | Levy et al. | 606/63 |
| 7,632,277 | B2 * | 12/2009 | Woll et al. | 606/86 R |
| 8,097,018 | B2 * | 1/2012 | Malandain et al. | 606/246 |
| 2002/0068939 | A1 | 6/2002 | Levy et al. | |
| 2002/0165544 | A1 * | 11/2002 | Perren et al. | 606/63 |
| 2003/0078581 | A1 * | 4/2003 | Frei et al. | 606/68 |
| 2006/0064094 | A1 | 3/2006 | Levy et al. | |
| 2010/0145396 | A1 * | 6/2010 | Thornes | 606/313 |

FOREIGN PATENT DOCUMENTS

| | | |
|---|---|---|
| EP | 2298201 A1 | 3/2011 |
| GB | 2268068 A | 1/1994 |

OTHER PUBLICATIONS

PCT International Search Report, Application No. PCT/US2013/039330, May 2, 2013.

* cited by examiner

Primary Examiner — Jan Christopher Merene
Assistant Examiner — Steven Cotroneo
(74) Attorney, Agent, or Firm — Nydegger & Associates

(57) ABSTRACT

An intraosseous device is disclosed that can be positioned to straddle a bone fracture to stabilize the fracture and provide structural support for the bone and the surrounding areas. The device includes wire assemblies that are deployable on each side of the fracture to anchor the device within the bone. For the device, an elongated tube is formed with a plurality of slots at each tube end. A central member is mounted inside the tube and moveable members are positioned inside the tube, one at each tube end. Wires connect the moveable members to the central member. A rod cooperates with each moveable member and is rotatable to draw each moveable member inwardly toward the central member. This forces each wire to bow and displace a central wire portion through a corresponding slot and into contact with the bone's inner wall to anchor the device in the bone.

20 Claims, 2 Drawing Sheets

INTRAOSSEOUS EXPANDABLE FIXATION DEVICE

FIELD OF THE INVENTION

The present invention pertains generally to medical devices for treating, bone injuries and disease. More specifically, the present invention pertains to internal bone fixation devices that are designed to stabilize an injured bone and provide structural support. The present invention is particularly, but not exclusively, useful as a fixation device that is positionable, within a bone, to treat a long bone fracture.

BACKGROUND OF THE INVENTION

The bones of the human skeleton serve many important structural and mechanical purposes. Among them, the bones protect organs, provide a frame to support the body; and function along with muscle and tissue to allow parts of the body to move. Unfortunately, bones are often subject to damage, for example, stress fractures due to high force impacts or bone loss due to osteoporosis or bone cancer.

Long bones are generally classified as bones that are longer than they are wide. Long bones in the human skeletal system include the femora, tibiae, fibulae, humeri, radii, ulnae, metacarpals, metatarsals, phalanges and the clavicles. Long bones are crucial for skeletal mobility and, due to their size and location on the body, account for the majority of bone fractures.

Healing of an injured bone involves natural processes. Typically, a fracture treatment regimen consists of restoring the fractured pieces of bone to their natural positions (if necessary), and maintaining those positions while the bone heals. Typically, this process involves aligning the bone portions into suitable positions to facilitate healing and verifying the improved alignment with an X-ray. Once the bone portions are in position to heal, the bone, surrounding tissue and adjacent joints can be stabilized to prevent movement and preserve anatomical alignment. Typically, the stabilization period varies depending on the type of injury. In some cases, only temporary stabilization is required. For example, some injuries may sufficiently heal in about 4-6 weeks. On the other hand, some injuries may require permanent stabilization.

Apparatus for stabilizing a bone can include plaster or fiberglass casts and metal splints. In addition, surgical nails, screws, plates and wires are often implanted surgically to directly hold the fractured bone together. Also, for some types of long bone fractures, external fixators have been employed. In some cases, permanent stabilization can be achieved by affixing a metal plate or rod directly to the exterior of a fractured bone, for example, using screws to attach the plate or rod to the bone. The plate or rod can then be left permanently implanted within the body to promote healing and add needed structural support to the damaged area.

In addition to the techniques described above, intramedullary rods have been used to stabilize bone injuries (and thereby promote healing) and add structural support. As the name implies, an intramedullary rod is a metal rod that is forced into the medullary cavity of a bone, typically a long bone, and affixed therein, typically using screws. The screws, however, can be damaging to the bone and can result in mechanical failure and/or biological incompatibility.

In light of the above, it is an object of the present invention to provide a device that can be implanted into a damaged bone to stabilize the bone and provide structural support for the bone and the surrounding areas. Another object of the present invention is to provide a device that can be positioned within a long bone to straddle a bone fracture with attachment points on each side of the bone fracture. Still another object of the present invention is to provide an intraosseous device positionable to straddle a bone fracture with attachment points that are relatively non-invasive to the bone structure. Yet another object of the present invention is to provide an intraosseous expandable fixation device that is easy to use, is relatively simple to manufacture, and is comparatively cost effective.

SUMMARY OF THE INVENTION

In accordance with the present invention, an intraosseous device that can be implanted inside a fractured bone to stabilize the fracture and provide structural support for the bone and the surrounding areas is provided. More specifically, the intraosseous device can be positioned within a bone to straddle a bone fracture. Once properly positioned inside the bone, wire assemblies contained in the device can be deployed on each side of the fracture to anchor the device within the bone.

In greater structural detail, the device includes an elongated tube having a tube wall that defines a central tube axis in the direction of tube elongation. At one end of the tube, a proximal tube portion is formed with a plurality of axially aligned slots that extend through the tube wall. At the other end, a distal tube portion is formed with a plurality of axially aligned slots that extend through the tube wall. For example, in one embodiment of the device, four slots are uniformly spaced around the circumference of the tube in both the proximal and distal portions.

Additionally, for the present invention, a hollow, central member is positioned inside the tube and affixed, to the tube wall between the proximal and distal tube portions. Also positioned inside the tube are a hollow proximal member and a hollow distal member. The proximal member is positioned in the tube adjacent to the proximal tube portion and the distal member is positioned in the tube adjacent to the distal tube portion. Both the proximal member and the distal member are disposed in the tube to allow axial movement of proximal and distal members within the tube.

To anchor the device to the bone on each side of a bone fracture, the device includes a plurality of proximal wires and a plurality of distal wires. Each proximal wire has a first end that is affixed to the central member and a second end that is affixed to the proximal member. Similarly, each distal wire has a first end that is affixed to the central member and a second end that is affixed to the distal member. Moreover, each proximal wire is aligned with a corresponding slot in the proximal tube portion and each distal wire is aligned with a corresponding slot in the distal tube portion. When the wires are in a relaxed state, they are substantially straight and extend in directions that are substantially parallel to the central tube axis.

In accordance with the present invention, an actuator rod is provided to move the proximal and distal members within the tube. With this movement, the wires deploy and anchor the device to the bone. In greater structural detail, an actuator rod includes a shaft that is threaded (e.g. with male threads) at a first shaft end and is formed with a head (e.g. bolt head) at a second shaft end. The threaded end of the rod is fed through the hollow proximal and central members to engage a set of threads (e.g. female threads) that are formed in the distal member. The rod is then threaded into the distal member until the rod head abuts the proximal member. At this point, continued rotation of the rod will cause the proximal and distal members to move inwardly toward the central member. This, in turn, will have an effect on the wires. More specifically, each wire will be forced to bow outwardly and displace a central wire portion away from the tube axis and through a corresponding slot formed in the tube.

In use, the intraosseous device is assembled with the proximal and distal members initially spaced from the central member at respective distances that allow the wires to be in a relaxed state (i.e. substantially straight). Next, the device is positioned within a bone, for example, in the medullary cavity of a long bone, with the proximal tube portion on one side of a bone fracture and the distal tube portion or the other side of the bone fracture. Once the device and bone are properly positioned, the actuator rod is rotated, for example, by inserting a narrow tool into a small opening formed in the bone. As described above, turning the actuator rod causes each wire to bow and extend a central portion of each wire through a corresponding slot. Further rotation of the actuator rod can be performed until each wire contacts and applies a suitable anchoring force against the inner wall of the bone to secure the device in the bone.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and, in which.

DESCRIPTION OF THE PREFERRED EMBODIMENTS

Figure 1:
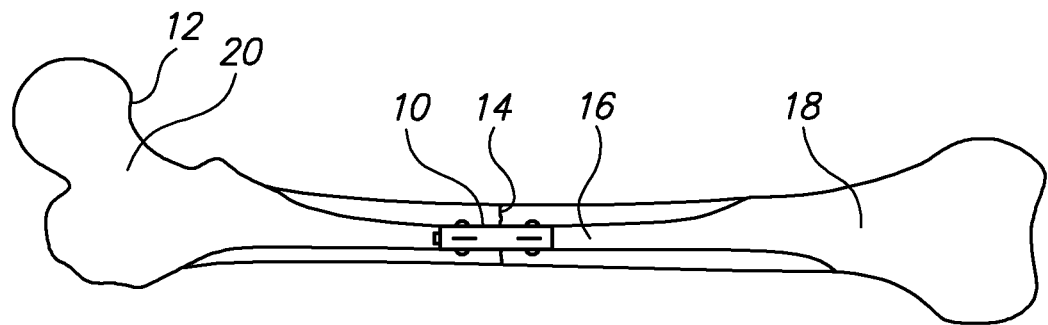
FIG. 1 is a sectional view showing an intraosseous expandable fixation device positioned to straddle a fracture in a femur bone in accordance with the present invention.

Referring initially to FIG. 1, a device 10 is shown operationally positioned in a long bone 12, which, for illustration purposes, is an adult femur bone 12 which has suffered a fracture 14. As shown in FIG. 1, the device 10 can be positioned within the bone 12 to straddle the bone fracture 14. Although the device 10 is shown positioned within the medullary cavity 16 of the bone 12, it is to be appreciated that other positions within the bone 12 may be suitable for employing the device 10 such as location 18 or location 20. Moreover, in spite of the fact that the device 10 may have certain advantages in treating fractured bones and/or being operationally positioned to straddle a fracture, it is to be appreciated that the device 10 can be useful for other purposes. For example, the device 10 may be used to provide support on one side of a fracture or to provide support in situations where bone loss or bone disease has occurred.

Figure 2:
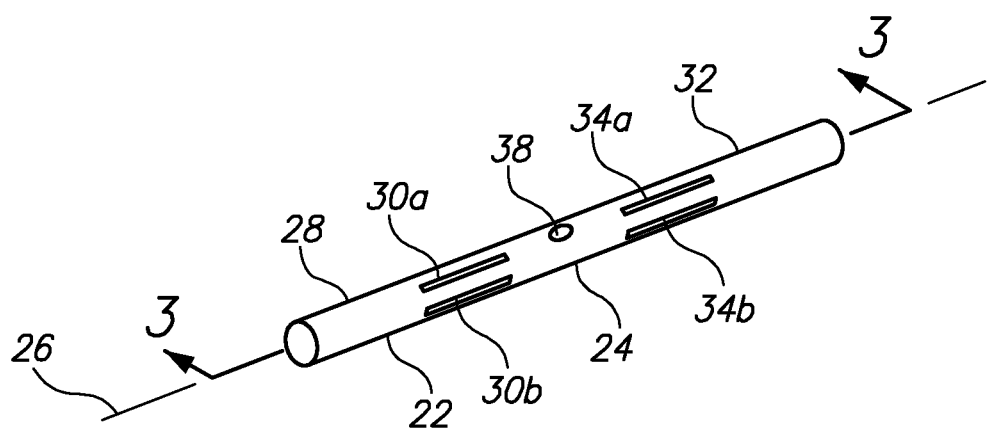
FIG. 2 is a perspective view of a portion of an intraosseous expandable fixation device shown with the deployable wires in their relaxed, stowed configuration.

Referring now to FIG. 2, a portion of the device 10 illustrated in FIG. 1 is shown. As seen there, the portion includes an elongated tube 22 having a tube wall 24 that defines a central tube axis 26 in the direction of tube elongation. It can further be seen that the tube 22 includes a proximal tube portion 28 that is formed with a plurality of axially aligned slots 30a,b that extend through the tube wall 24. The tube 22 also includes a distal tube portion 32 that is formed with a plurality of axially aligned slots 34a,b that extend through the tube wall 24. For the exemplary embodiment shown, four slots are uniformly spaced around the circumference of the tube 22 (i.e. ninety degrees apart) in the proximal portion 28 and four slots are uniformly spaced around the circumference of the tube 22 in the distal portion 32. Although an embodiment with four slots in each portion is shown and described, it is to be appreciated that more than four slots per portion and as few as one slot per portion may be used. Moreover, the slots do not necessarily need to be uniformly spaced around the circumference of the tube 22 for suitable operation.

Figure 3:
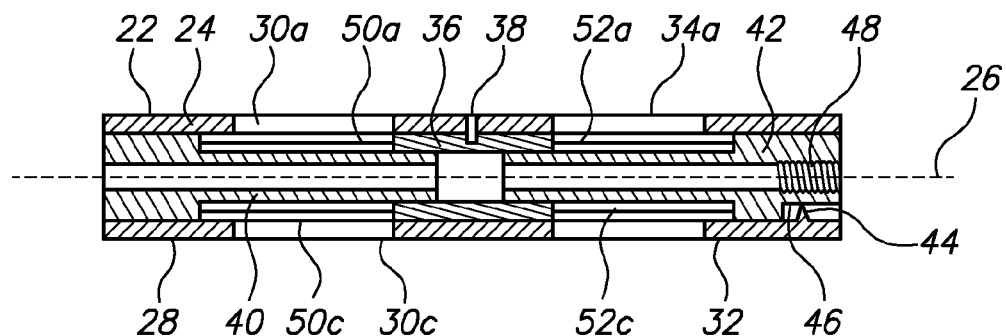
FIG. 3 is a cross sectional view of the intraosseous expandable fixation device portion shown in FIG. 2 as seen along line 3-3 in FIG. 2.

Cross referencing FIGS. 2 and 3, it can be seen that, a hollow, central member 36 is positioned inside the tube and affixed to the tube wall 24 via pin 38 between the proximal portion 28 and distal portion 32. Other attachment means such as adhesive bonding may be used. As shown, the central member 36 can be shaped as a hollow cylinder with an outside diameter that is approximately equal to the inside diameter of the tube 22.

Continuing with FIG. 3, it can be seen that a hollow proximal member 40 and a hollow distal member 42 are positioned inside the tube 22. Specifically, the proximal member 40 is positioned in the tube 22 adjacent to the proximal tube portion 28 and the distal member 42 is positioned in the tube 22 adjacent to the distal tube portion 32. Both the proximal member 40 and the distal member 42 are disposed in the tube 22 to allow axial movement of the proximal member 40 and the distal member 42 within the tube 22. As shown, the proximal member 40 and the distal member 42 can each have portions shaped as hollow cylinders with an outside diameter that is approximately equal to the inside diameter of the tube 22. In addition, a key 44 that is formed on the tube wall 24 can ride in a groove 46 that is formed in distal member 42 to prevent rotation of the distal member 42 within the tube 22 while allowing axial movement of the distal member 42. A similar rotation prevention means (not shown) can be provided to prevent rotation of proximal member 40 (while allowing axial, movement). It can also be seen that the distal member 42 is formed with a set of internal threads 48 (e.g. female threads).

Continuing with FIG. 3, it can be seen that a plurality of proximal wires 50a, 50c are provided with each proximal wire having a first end that is affixed to the central member 36 and a second end that is affixed to the proximal member 40. For this purpose, any attachment method known in the pertinent art for attaching a wire to a structure can be used. Also shown, a plurality of distal wires 52a, 52c are provided with each distal wire having a first end that is affixed to the central member 36 and a second end that is affixed to the distal member 42. FIG. 3 shows that each wire 50a, 50c, 52a, 52c is aligned with a corresponding slot 30a, 30c, 34a, 34c, respectively.

Figure 4:
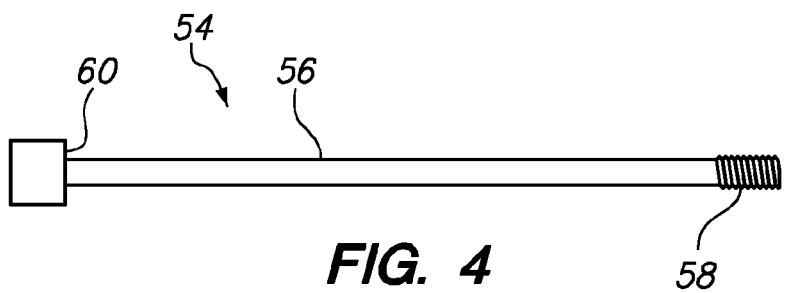
FIG. 4 is a plan view of an actuator rod.

FIG. 4 shows an actuator rod 54 for use with the structure shown in FIG. 3. As shown in FIG. 4, the actuator rod 54 includes a shaft 56 having a set of external threads 58 (i.e. with male threads) that are formed in the shaft 56 at one end. As detailed further below, the external threads 58 are shaped and sized to achieve successful mating with internal threads 48, thus, allowing the actuator rod 54 to engage the distal member 42. FIG. 4 further shows that the actuator rod 54 includes an abutment head 60, which as shown in FIG. 5, can be formed with a hexagonal shaped recess 62 (other shapes may be used) allowing a complementary tool to fill recess 62 and rotate the actuator rod 54.

Figure 5:
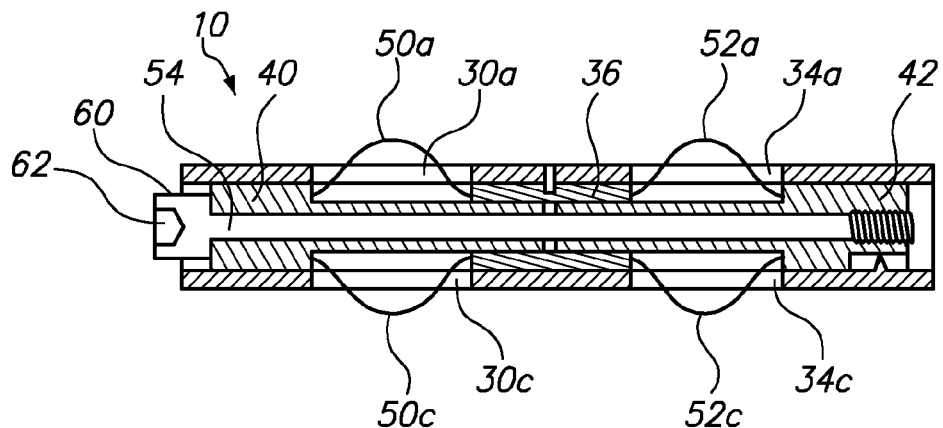
FIG. 5 is a cross sectional view of the intraosseous expandable fixation device including the actuator rod, as seen along line 3-3 in FIG. 2, and with the wires in their deployed configuration.

As best seen in FIG. 5, to assemble the device 10, the threaded end of the rod 54 is fed through the hollow proximal member 40 and central member 36 to engage internal threads 48 formed in the distal member 42. Once the threads 48, 58 are engaged, the rod 54 is rotated until the rod head 60 abuts the proximal member 40. At this point, the device 10 is assembled and can be implanted into a bone.

In the assembled configuration and prior to implantation, the wires 50a, 50c, 52a, 52c are in their initial, stowed configuration as shown in FIG. 3. In this configuration, the proximal member 40 and distal member 42 are spaced from the central member 36 at respective distances that allow the wires 50a, 50c, 52a, 52c to be in a relaxed state. As further shown in FIG. 3, when the wires 50a, 50c, 52a, 52c are in a relaxed state, they are substantially straight and extend in directions that are substantially parallel to the central tube axis 26.

With the device 10 assembled and the wires 50a, 50c, 52a, 52c in a relaxed state, the device 10 can be positioned within a bone. Comparing FIGS. 1 and 3, it can be seen that when the device 10 is properly positioned within a bone 12, the proximal tube portion 28 is positioned on one side of bone fracture 14 and the distal tube portion 32 is positioned on the other side of bone fracture 14. Once the device 10 and bone 12 are properly positioned and aligned, the wires 50a, 50c, 52a, 52c can be deployed to anchor the device 10 in the bone 12.

To deploy the wires 50a, 50c, 52a, 52c, the actuator rod 54 is rotated, for example, by inserting a narrow tool (not shown) into a small opening formed in the bone 12. Deployment of the wires 50a, 50c, 52a, 52c can best be appreciated by comparing FIG. 3 (stowed wires) and FIG. 5 (deployed wires). As shown there, rotation of the actuator rod 54 causes the proximal member 40 and distal member 42 to move inwardly along the axis 26 toward the central member 36. The effect of this is that the straight line distance between the ends of each wire 50a, 50c, 52a, 52c is decreased. As best seen in FIG. 5, during rotation of the actuator rod 54, each wire 50a, 50c, 52a, 52c bows outwardly and a central wire portion moves radially from the tube axis 26 and through a corresponding slot 30a, 30c, 34a, 34c formed in the tube wall 24. Rotation of the actuator rod 54 can be continued until each wire 50a, 50c, 52a, 52c contacts and applies a suitable anchoring force against the inner wall of the bone 12 to secure the device 10 in the bone 12.

For the device 10, the wires are typically made of a biocompatible material such as a titanium alloy or other biocompatible metal. Additionally, the other components described above are preferably constructed of rigid biocompatible metal such as titanium alloys.

Those skilled in the pertinent art will appreciate that several variations of the above described embodiments are clearly within the scope of the present invention. For example, an embodiment can be constructed in which the proximal and distal members are stationary and two central members are axially moveable to bow the wires. To achieve movement of the central members, two actuator rods may be used or a single rod having two sets of threads that are spaced apart along the rod shaft (e.g. one left hand threadset and one right hand threadset). In another variation, a different technique known in the art for controllably adjusting the axial spacing of two members (i.e. the proximal and distal, members) may be used.

While the particular Intraosseous Expandable Fixation Device as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. An intraosseous device for stabilizing and structurally supporting a bone having a bone fracture, said device comprising:
an elongated tube having a wall and defining an axis and having a proximal portion with an axially aligned slot formed through the wall and a distal portion with an axially aligned slot formed through the wall;
a hollow, central member positioned inside said tube and affixed to the tube wall;
a hollow distal member positioned in said tube for axial movement therein, said distal member formed with internal threads;
a hollow proximal member positioned in said proximal portion of said tube for axial movement therein;
at least one proximal wire interconnecting the central member with the proximal member and at least one distal wire interconnecting the central member with the distal member; and
a threaded actuator rod for passing through said proximal, central and distal members to engage said internal threads and rotatable to slide said proximal and distal members toward said central member to move said proximal and distal wires from a first substantially straight configuration to a second bowed configuration wherein the proximal and distal wires extend through the proximal and distal slots, respectively, to anchor the device in the bone.

2. A device as recited in claim 1 wherein said hollow central member is affixed to said tube by a pin.

3. A device as recited in claim 1 wherein said tube is cylindrical.

4. A device as recited in claim 1 further comprising a means for preventing said hollow distal member from rotating in said tube.

5. A device as recited in claim 1 wherein said proximal portion axially aligned slot is a first proximal portion axially aligned slot and further comprising a second proximal portion axially aligned slot, and wherein said at least one proximal wire includes first and second proximal wires.

6. A device as recited in claim 1 wherein said proximal and distal wires are substantially parallel to said axis in said first substantially straight configuration.

7. A device as recited in claim 1 wherein said actuator rod includes a shaft having a threaded portion and a head.

8. A device as recited in claim 1 wherein said distal and proximal wires are made of a titanium alloy.

9. A device as recited in claim 1 wherein said tube is cylindrical and has an inner diameter, d, and said proximal member has a cylindrical portion having an outer diameter, D, with d substantially equal to D.

10. An intraosseous device for straddling a bone fracture to stabilize and structurally support the bone, said device comprising:
a tube having a wall formed with a first slot formed through the wall at a first tube end and a second slot formed through the wall at a second tube end;
a fixed member positioned inside said tube and affixed to said tube wall;
a threaded member positioned in said tube for axial movement therein;
a non-threaded member positioned in said tube for axial movement therein;

a first wire interconnecting the fixed member with the threaded member and a second wire interconnecting the fixed member with the non-threaded member; and an actuator having threads for engagement with said threaded member and a head for engagement with said non-threaded member to move said threaded and non-threaded members relative to the fixed member and reshape said first and second wires from a first stowed configuration to a second anchoring configuration wherein the wires extend through the slots, respectively, to affix the device to the bone.

11. A device as recited in claim 10 wherein said threaded member is formed with internal threads and said actuator rod includes a shaft having an internally threaded portion.

12. A device as recited in claim 10 wherein said fixed member is a single fixed member.

13. A device as recited in claim 10 wherein said one fixed member is positioned between said threaded and non-threaded members.

14. A device as recited in claim 10 wherein said first and second wires are made of a titanium alloy.

15. A device as recited in claim 10 wherein said tube is elongated and defines an axis and first and second wires are substantially parallel to said axis in said first stowed configuration.

16. A method for anchoring a device within a bone having a bone fracture to stabilize and structurally support the bone, said method comprising the steps of:

positioning a central member in a tube, the tube formed having a wall with a proximal slot and a distal slot formed through the wall;

affixing said central member to said tube wall;

positioning a proximal member and a distal member in said tube for axial movement therein;

interconnecting the central member and the proximal member with a proximal wire and the central member and the distal member with a distal wire;

positioning the device in a bone with the proximal wire on one side of the bone fracture and the distal wire on the other side of the fracture; and urging said proximal and distal members toward each other to reshape said proximal and distal wires from a first stowed configuration to a second anchored configuration wherein the proximal and distal wires extend through the proximal and distal slots, respectively, to affix the device to the bone.

17. A method as recited in claim 16 wherein said positioning step positions the device in the medullary cavity of a bone.

18. A method as recited in claim 17 wherein the bone is a long bone.

19. A method as recited in claim 16 wherein said tube is cylindrical.

20. A method as recited in claim 16 wherein said wires are made of a titanium alloy.

\* \* \* \* \*